United States Patent [19]
Lin

[11] Patent Number: 6,013,078
[45] Date of Patent: Jan. 11, 2000

[54] SECURING DEVICE FOR BONE FASTENER

[76] Inventor: Chin Lin, Department of Orthopaedic Surgery national Taiwan University Hospital 7, Chung Shan S. Road, Taipei, Taiwan

[21] Appl. No.: 09/136,266

[22] Filed: Aug. 19, 1998

[51] Int. Cl.⁷ .................................................. A61B 17/56
[52] U.S. Cl. ................................................ 606/72; 606/73
[58] Field of Search .................................. 606/72, 73, 62, 606/64, 65, 66; 411/294, 295, 300

[56] References Cited

U.S. PATENT DOCUMENTS

| | | | |
|---|---|---|---|
| 2,624,386 | 1/1953 | Russel | 151/41.73 |
| 5,032,125 | 7/1991 | Durham et al. | 606/62 |
| 5,662,653 | 9/1997 | Songer et al. | 606/61 |

*Primary Examiner*—Michael Buiz
*Assistant Examiner*—Daphna Shai
*Attorney, Agent, or Firm*—Ezra Sutton

[57] ABSTRACT

A securing device for bone fastener is provided, which allows the bone fastener to be more securely fixed in position in the fractured bone. The securing device includes a bolt having an elongated portion and a head portion, with the head portion being formed with a threaded through hole which is inclined with respect to the longitudinal axis of the bolt. Moreover, the securing device includes a set screw having a threaded portion which can screw into the threaded through hole in the bolt and which is greater in length than the threaded through hole. In use, the elongated portion of the bolt is inserted through the implantation hole and the opening in the fractured bone; then a hole is drilled through the inclined through hole in the head portion of the bolt; and finally the set screw is screwed through the inclined hole in the head portion of the bolt into the hole in the fractured bone. This allows the securing device to be fixed in position in the fractured bone, thus securing the bone fastener fixedly in position.

14 Claims, 1 Drawing Sheet

SECURING DEVICE FOR BONE FASTENER

BACKGROUND OF THE INVENTION

1. Field of the Invention

This invention relates to a securing device, and more particularly, to a securing device for bone fastener, which allows the bone fastener to be more reliably fixed in position in fractured bones.

2. Description of Related Art

A bone fastener can be implanted inside fractured bones so as to allow the fractured parts to be fastened together. When implanted inside fracture bones, the bone fastener is secured in position by means of threaded bolts so as to prevent the bone fastener from sliding in the fracture bones. Conventional securing means, however, are still unsatisfactory to provide reliable securing effect to the bone fastener, in that the bolt tends to slip out of the fractured bone that is associated with osteoporosis. Moreover, the threaded bolt can nevertheless cause stress to concentrate at the threaded portion, thus causing the bolts to be easily to break. These reasons make conventional securing means unsatisfactory in use.

SUMMARY OF THE INVENTION

It is therefore an objective of the present invention to provide a securing device for bone fastener, which can allow the bone fastener to be more reliably secured in position in fractured bones.

It is another objective of the present invention to provide a securing device for bone fastener, which includes a bolt that would not be easily to break.

It is still another objective of the present invention to provide a securing device for bone fastener, which would less easily cause the implantation hole in the fractured bone to break.

In accordance with the foregoing and other objectives of the present invention, a securing device for bone fastener is provided. The securing device of the invention includes the following constituent parts:

(a) a bolt having an elongated portion and a head portion, with the head portion being formed with a threaded through hole which is inclined with respect to the longitudinal axis of the bolt; and (b) a set screw having a threaded portion which can screw into the threaded through hole in the bolt and which is greater in length than the threaded through hole.

BRIEF DESCRIPTION OF DRAWINGS

The invention can be more fully understood by reading the following detailed description of the preferred embodiments, with reference made to the accompanying drawings, wherein.

DETAILED DESCRIPTION OF PREFERRED EMBODIMENTS

Figure 1:
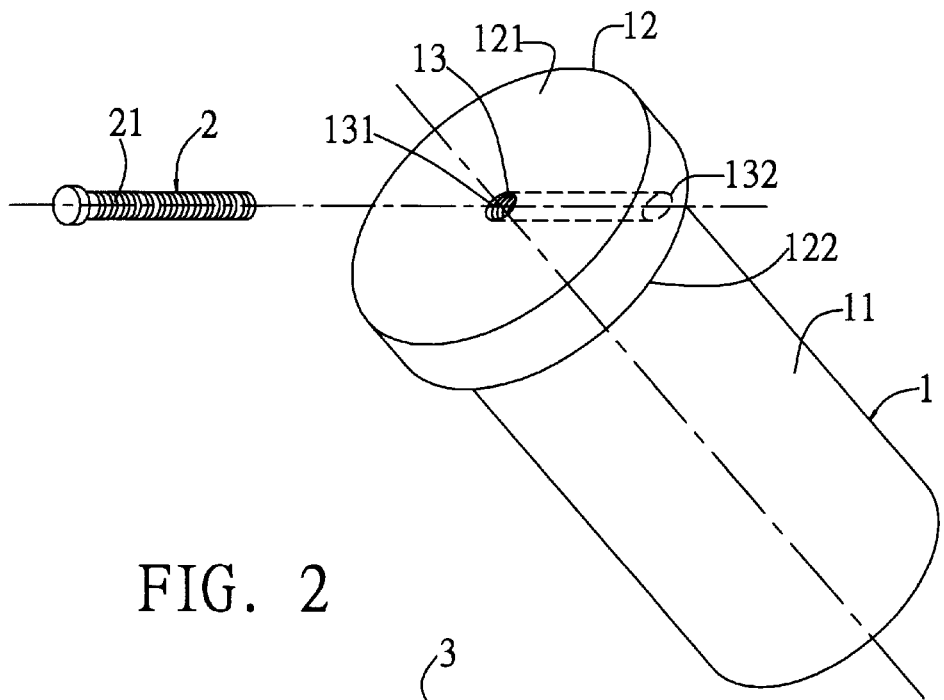
FIG. 1 is an exploded perspective view of the securing device for bone fastener according to the invention.

FIG. 1 is an exploded perspective view of the securing device for bone fastener according to the invention. As shown, the securing device of the invention includes two main parts: a bolt 1 and a set screw 2. The bolt 1 has an elongated portion 11 and a head portion 12. The head portion 12 is formed with a threaded through hole 13 therein. The threaded through hole 13 is inclined with respect to the longitudinal axis of the bolt 1, having a first opening end 131 on the top side 121 of the head portion 12 and a second opening end 132 on the bottom side 122 of the head portion 12. The set screw 2 has a threaded portion 21 which can be screwed into the threaded through hole 13 and which is greater in length than the threaded through hole 13.

Figure 2:
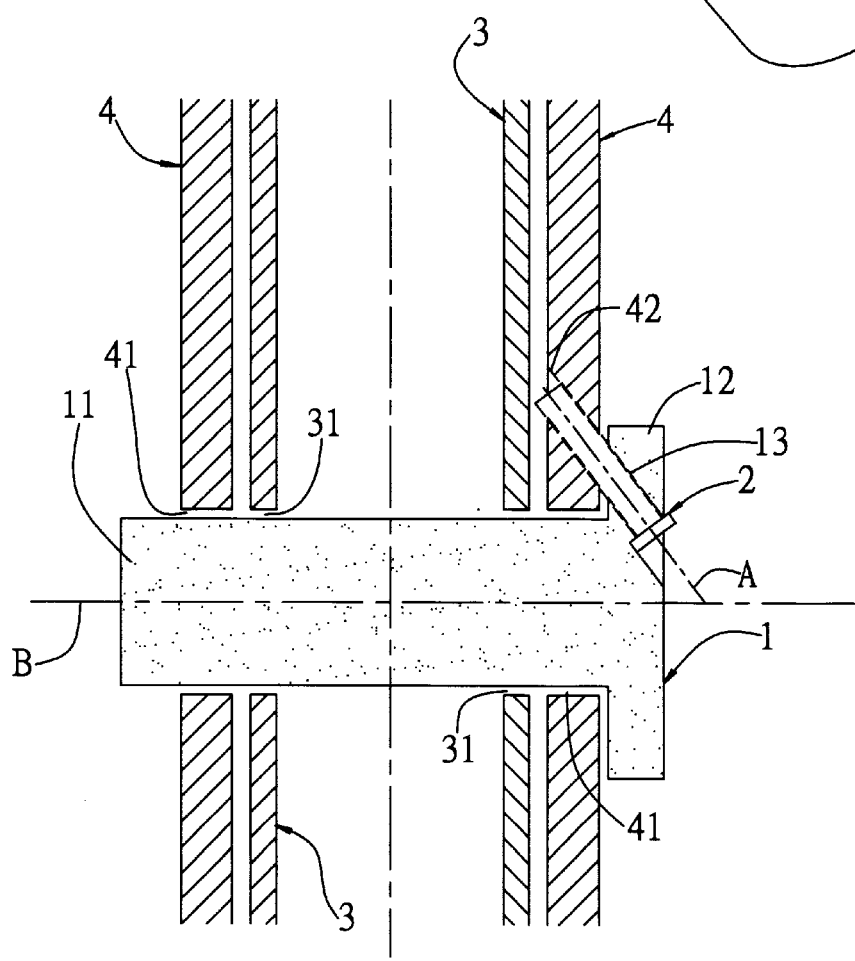
FIG. 2 is a sectional view of the securing device of the invention when used to secure a bone fastener fixedly in position in a fractured bone.

FIG. 2 is a sectional view of the securing device of the invention when used to secure a bone fastener 3 fixedly in position in a fractured bone 4. The bone fastener 3 has an implantation hole 31. To use the securing device, the procedure includes a first step of providing an opening 41 in the fractured bone 4 at a location where the implantation hole 31 is formed; a second step of inserting the elongated portion 11 of the bolt 1 through the opening 41 and the implantation hole 31 into the bone fastener 3 until the head portion 12 is stopped by the outer surface of the fractured bone 4; a third step of a hole 42 in the fractured bone 4 through the threaded through hole 13 in the head portion 12 of the bolt 1; and a fourth step of screwing the screw 2 through the threaded through hole 13 into the hole 42 in the fractured bone 4. Since the set screw 2 is greater in length than the threaded through hole 13, its front end can insert into the hole 42, thereby allowing the screw 2 to be secured by the hole 42 and further allowing the bolt 1 to be securely fixed in position to secure the bone fastener 3 in the fractured bone 4 in position.

Since the set screw 2 is inclined with respect to the bone 4, the set screw 2 can be more deeply screwed into the bone 4 (i.e., the hole 42 can be formed with a greater depth to provide a greater securing effect to the screw 2). As a result, the set screw 2 can provide a more reliable securing effect to the bolt 1 which can more reliably secure the bone fastener 3 in the fractured bone 4 in position.

In other preferred embodiment, the threaded through hole 13 can be formed in a number of two or more, which are used in conjunction with two or more set screws to provide an even more reliable securing effect to the bone fastener. It is a characteristic feature of the invention that the elongated portion 11 of the bolt 1 is unthreaded. The cross section of the elongated portion 11 can be either circular, elliptical, triangular, square, or any polygonal shapes. Moreover, the elongated portion 11 can be either entirely or partly threaded with a low pitch, allowing the elongated portion 11 to be screwed to the implantation hole 31 and the opening 41 in the fractured bone 4. Additional, the head of the set screw 2 can be either above the head of bolt 1 or sunk in the head of bolt 1.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A securing device for bone fastener in a fractured bone, which comprises:

a bolt having an elongated portion and a head portion, with the head portion being formed with a threaded through hole which is inclined with respect to the longitudinal axis of the bolt; and a screw having a threaded portion which can screw into the threaded through hole in the bolt and which is greater in length than the threaded through hole.

2. The securing device of claim 1, wherein the elongated portion is unthreaded.

3. The securing device of claim 2, wherein the elongated portion of the bolt has a circular cross section.

4. The securing device of claim 2, wherein the elongated portion of the bolt has a polygonal cross section.

5. The securing device of claim 4, wherein the elongated portion of the bolt has a triangular cross section.

6. The securing device of claim 4, wherein the elongated portion of the bolt has a square cross section.

7. The securing device of claim 2, wherein the elongated portion of the bolt has an elliptical cross section.

8. The securing device of claim 1, wherein the elongated portion of the bolt is entirely threaded.

9. The securing device of claim 1, wherein the elongated portion of the bolt is partly threaded.

10. The securing device of claim 1, wherein the threaded through hole has a first opening end on a top side of the head portion and a second opening end on a bottom side of the head portion.

11. The securing device of claim 1, wherein the head portion of the bolt is circular in shape.

12. The securing device of claim 1, wherein the head portion of the bolt is polygonal in shape.

13. The securing device of claim 1, wherein said screw is a set screw which is partially threaded.

14. The securing device of claim 1, wherein said screw is a set screw which is totally threaded.

* * * * *